United States Patent [19]

Michaels et al.

[11] Patent Number: 4,473,449
[45] Date of Patent: Sep. 25, 1984

[54] FLOWTHROUGH ELECTROCHEMICAL HEMODIALYSATE REGENERATION

[75] Inventors: Alan S. Michaels, New York, N.Y.; Anthony J. Appleby, Mountain View, Calif.; Jeremy C. Wright, Round Lake, Ill.

[73] Assignee: The Board of Trustees of the Leland Stanford Junior University, Stanford, Calif.

[21] Appl. No.: 421,667

[22] Filed: Sep. 22, 1982

[51] Int. Cl.³ .............................................. C25B 1/26
[52] U.S. Cl. .................................... 204/101; 204/128; 204/129; 210/648; 210/748
[58] Field of Search ............... 210/639, 646, 647, 648, 210/748, 195.2, 257.2, 321, 927; 204/177, 180 R, 186, 299 R, 302, 101, 128, 129

[56] References Cited

U.S. PATENT DOCUMENTS

| | | | |
|---|---|---|---|
| 3,157,468 | 11/1964 | Kennedy et al. | 204/177 X |
| 3,617,545 | 11/1971 | Dubois | 210/648 X |
| 3,878,564 | 4/1975 | Yao et al. | 210/321.4 X |
| 3,909,377 | 9/1975 | Bizot et al. | 210/647 X |
| 3,930,982 | 1/1976 | Batha et al. | 204/299 R |
| 3,994,799 | 11/1976 | Yao et al. | 210/321.2 X |
| 4,347,110 | 8/1982 | Joyce et al. | 204/186 X |
| 4,388,163 | 6/1983 | Richter et al. | 204/101 |

FOREIGN PATENT DOCUMENTS

| | | | |
|---|---|---|---|
| 2342633 | 3/1975 | Fed. Rep. of Germany | 210/648 |
| 1397324 | 1/1975 | United Kingdom | 210/648 |

*Primary Examiner*—David R. Sadowski
*Attorney, Agent, or Firm*—Townsend and Townsend

[57] ABSTRACT

An improved method and electrolytic cell for the oxidation of nitrogen-containing waste materials in a dialysate stream used for hemodialysis, hemofiltration or peritoneal dialysis comprises a cylinder having a porous anode and a porous cathode spaced apart in the direction of flow. By flowing the spent dialysate in the direction from the anode to the cathode, and applying sufficient voltage to oxidize chloride ion present to activated chlorine, the waste materials are oxidized to chlorinated intermediates. In the vicinity of the cathode, the chlorinated intermediates react further to yield to nitrogen and carbon dioxide, with the chlorine being reduced back to chloride ion. In this way, the dialysate is regenerated without the net evolution of undesirable chlorine species.

13 Claims, 7 Drawing Figures

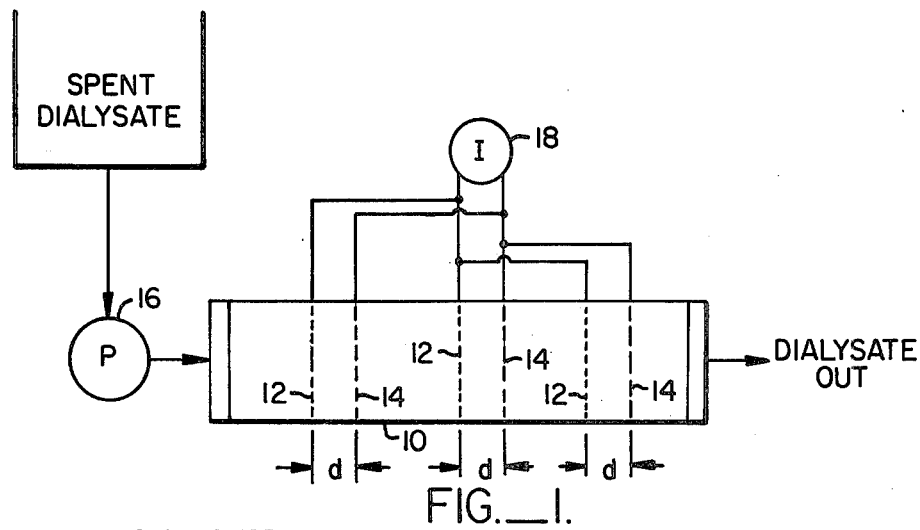
FIG._1.
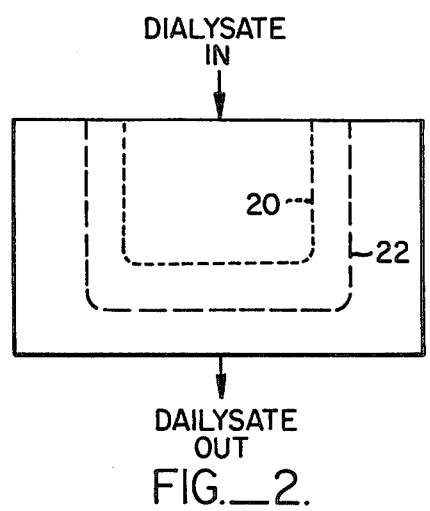
FIG._2.
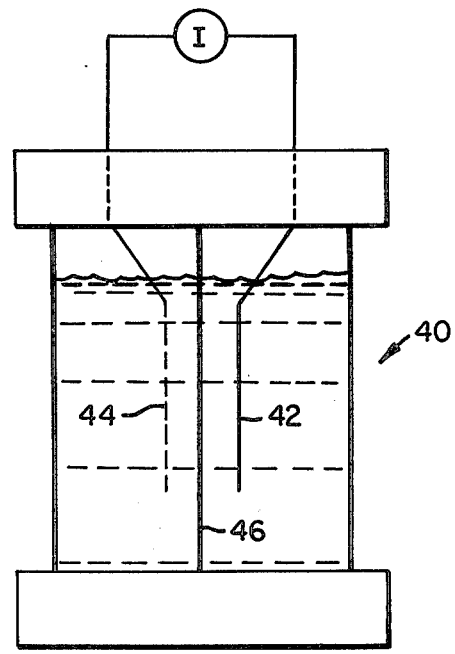
FIG._4.
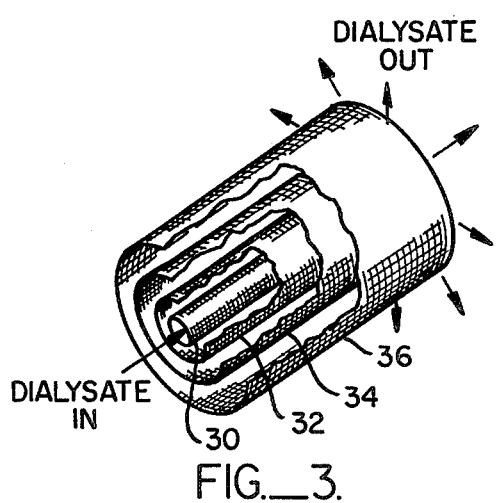
FIG._3.

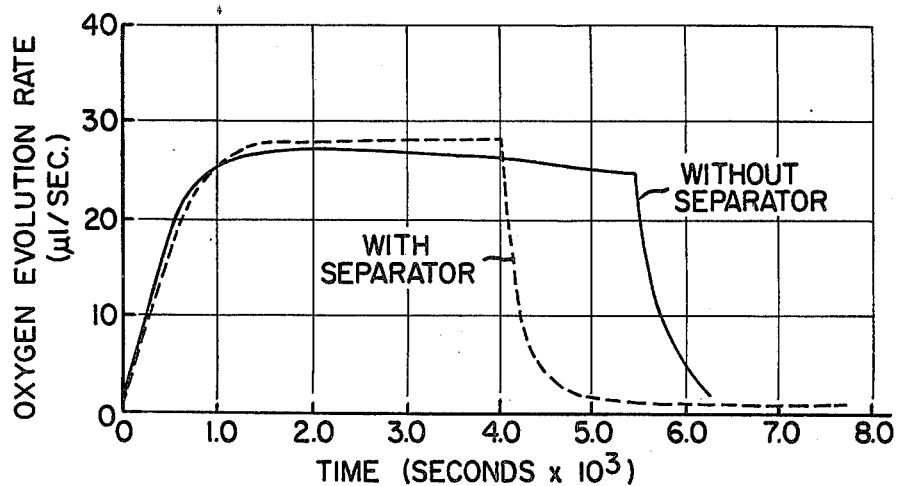
FIG._5.
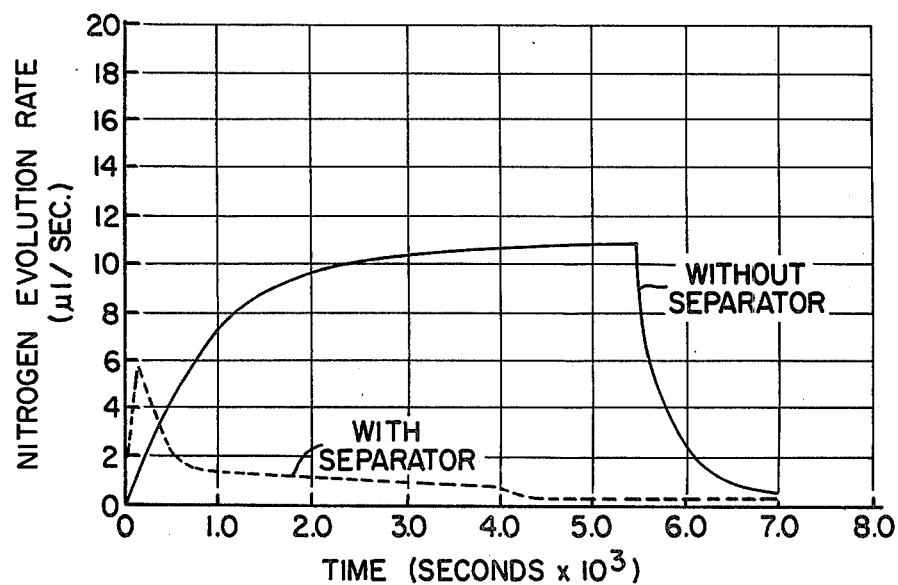
FIG._6.

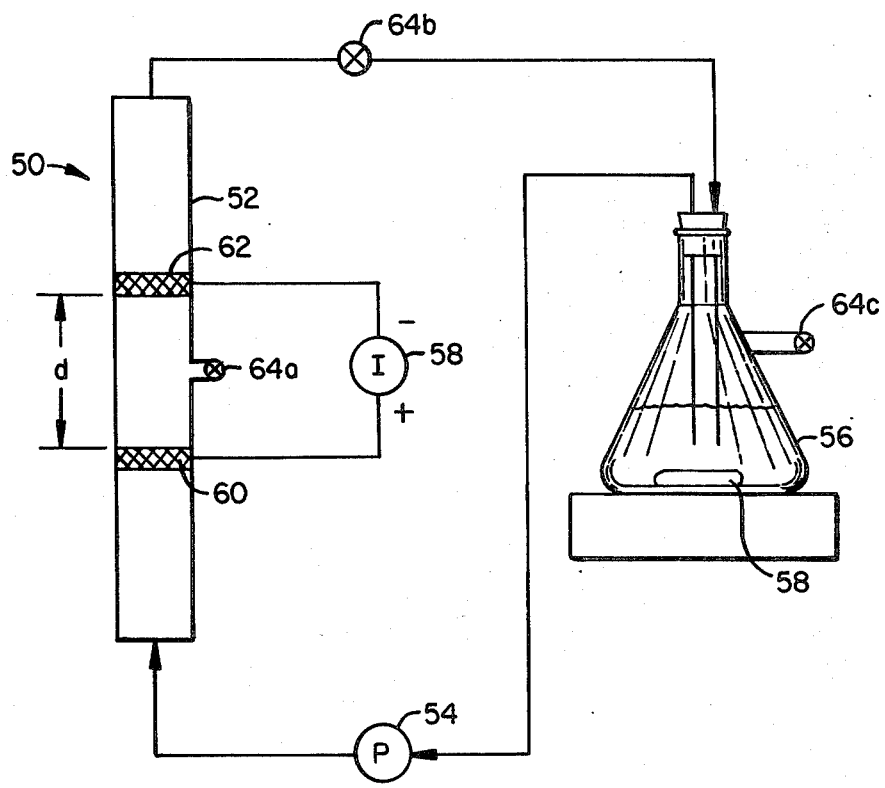
FIG._7.

FLOWTHROUGH ELECTROCHEMICAL HEMODIALYSATE REGENERATION

BACKGROUND OF THE INVENTION

1. Field of the Invention

The present invention relates generally to the regeneration of spent dialysate used in the treatment of kidney failure by hemodialysis, hemofiltration, peritoneal dialysis and the like, and more particularly to regeneration by electrolytic oxidation of the major nitrogen-containing organic waste materials removed from the blood.

Hemodialysis accomplishes removal of waste substances, principally urea, uric acid and creatinine, from the circulating blood by dialysis. The dialysate is an aqueous, saline solution prepared with appropriate concentrations of the essential blood salts which are not to be removed. The performance of a single hemodialysis treatment requires approximately 100 liters of dialysate. Hemofiltration and continuous ambulatory peritoneal dialysis similarly require large amounts of dialysate. The preparation of such large amounts of dialysate is both inconvenient and expensive. The need to provide such a large volume is particularly troublesome when using a portable dialysis unit in the patient's home or other location remote from a large source of dialysate. It is therefore desirable to provide a convenient safe method for regenerating spent dialysate to be used in conjunction with hemodialysis, hemofiltration, and peritoneal dialysis systems to reduce the total volume of dialysate required.

2. Description of the Prior Art

Various systems have been proposed for adsorbing or degrading the waste materials present in the circulating dialysate in a hemodialysis unit. Electrolysis of the dialysate above the chloride discharge potential to produce sodium hypochlorite which in turn oxidizes the waste materials is described in British Pat. No. 1,397,324. Wright, "An Investigation of Electrode Materials for Urea Electro-Oxidation," Engineer's Thesis, Stanford University (1980) discloses the use of ruthenium oxide-titanium oxide electrodes in regenerating spent dialysate by electrolytic oxidation. The use of electrolytic cells to oxidize the waste materials in the blood in vivo is described in U.S. Pat. Nos. 3,878,564 and 3,994,799 to Yao et al.

SUMMARY OF THE INVENTION

The present invention provides a method for regenerating dialysate by oxidizing the nitrogen-containing organic wastes removed from the blood during hemodialysis, hemofiltration, or peritoneal dialysis. The method employs an electrolytic flow cell wherein the anode and cathode are spaced apart in the direction of flow with the anode upstream of the cathode. By maintaining a potential difference across the cell such that the anode is maintained above the chloride discharge potential and hydrogen is evolved at the cathode, the waste products are oxidized and hydrolyzed to carbon dioxide and nitrogen. After passage through the cell, the regenerated dialysate is ready to be reused for hemodialysis and, in particular, is free from chlorine and other oxidized chlorine species. The method is an economical and energy-efficient technique for regenerating dialysate and is particularly convenient when used to reduce the total volume of dialysate required by a portable dialysis unit.

BRIEF DESCRIPTION OF THE DRAWINGS

FIG. 1 illustrates the preferred embodiment of the electrolytic cell of the present invention.

FIG. 2 illustrates a first alternate embodiment of the electrolytic cell.

FIG. 3 illustrates a second alternate embodiment of the electrolytic cell.

FIG. 4 illustrates the non-flow cell employed in Experiment 1.

FIGS. 5 and 6 are graphs illustrating the results of Experiment 1.

FIG. 7 is a flow sheet illustrating the experimental set up of Experiment 2.

DESCRIPTION OF THE SPECIFIC EMBODIMENTS

The system of the present invention comprises a flow cell having a chamber which defines a flow path for the spent dialysate. At least one anode and one cathode are provided inside the chamber, and the anode and cathode are spaced apart in the direction of flow so that the dialysate first passes the anode and thereafter passes the cathode. In addition to the flow cell, means for circulating the dialysate through the flow cell and a power supply for maintaining a potential difference across the anode and cathode are provided. The system may form an integral part of a hemodialysis unit wherein the dialysate is continuously regenerated during the performance of dialysis. Alternatively, the system can be used separately to regenerate a pool of spent dialysate which is collected during performance of one or more individual dialyses.

Referring to FIG. 1, the chamber of the flow cell will typically be conduit 10 defining a flow path for the dialysate. As illustrated, the flow path is linear and the cross section of the conduit is cylindrical, but non-linear flow paths and other cross-sections may be used. The dimensions of the conduit depend upon the expected flow rate of the dialysate therethrough and on the type of electrodes employed. Generally, the cross-sectional area of the conduit should be chosen to pass the desired flow rate of dialysate without excessive pressure drop. The electrodes and the conduit should also be sized based on the desired local current density and the expected oxidation rate of the waste metabolities.

An anode 12 is arranged upstream of a cathode 14. Often it will be desirable to provide more than one anode-cathode pair in series in the flow path in order to assure substantially complete degradation of the nitrogen-containing organic wastes. FIG. 1 illustrates three such pairs, although the number of pairs can vary. The optimal number of anode-cathode pairs will depend on the flow rate, electrode efficiency, current density and other factors which affect the performance of the individual pairs.

The spacing d between the anode and cathode of each pair is chosen by optimizing the following factors. The anode and cathode should be spaced sufficiently close to reduce the IR drop therebetween in order to reduce current usage. Conversely, the spacing must be sufficiently far to (1) prevent short-circuiting, and (2) provide sufficient time for the chemical reactions associated with degradation of the wastes. Typically, the spacing d should be at least 0.1 cm, preferably in the range from 0.1 to 1.0 cm.

It may also be desirable to provide more than one flow cell in parallel, depending on the expected flow rate of dialysate to be regenerated. For a given flow rate, the optimal number of parallel cells will generally depend on loss of efficiency as the diameter of the cell is increased.

Both the anode and cathode must be configured to assure substantially complete contact between the dialysate and the electrode as the dialysate flows through the cell. Wire mesh and solid flow-by electrodes which extend across the dialysate flow path are suitable. Preferred are porous, flow-through electrodes, typically comprising a sintered metal substrate coated with metal oxides, which promote substantially complete oxidation of the species of interest.

The present invention is not limited to any particular cell configuration, and in particular is not limited to linear flow patterns and series placement of the anode and cathode. Alternate arrangements include concentric, flow-through "thimbles" as illustrated in FIG. 2 where an anode 20 is nested inside the cathode 22. FIG. 3 illustrates porous anodes 30, 34 and cathodes 32, 36 arranged as concentric cylinders where the flow enters axially and passes radially outward through the electrodes.

The anode material must be stable at and above the chloride discharge potential as well as be resistant to attack by activated chlorine species generated by oxidation by the chloride ion. Suitable materials include platinum, and other stable platinum group metals, stable noble metal oxides, mixed stabilized nobel metal oxides (such as $RuO_2/TiO_2$ or $RuO_2/SnO_2/TiO_2$), graphite, and certain other carbons.

The anode of choice is a dimensionally stable anode consisting of a layer of ruthenium oxide and titanium oxide deposited on a solid titanium support. Other metal oxides, such as a tin oxide, may be included in the film. Such an electrode may be prepared by coating porous, sintered titanium (65% porosity, 25 micron mean pore diameter) with a solution of $RuCl_3.3H_2O$ (19 mole %), $SnCl_2$ (13 mole %) and $Ti(OBu)_4$ (68 mole %) in butyl alcohol and hydrochloric acid. The coating solution is applied repeatedly, and after each application the electrode is heated to 450° C. for about from five to seven minutes to produce a film of ruthenium oxide, titanium oxide and tin oxide at the electrode surface. See, Ger. Offen. No. 2,342,633, the disclosure of which is incorporated herein by reference.

The choice of cathode material is less critical. Suitable materials include platinum, nickel, cadmium, tin, stainless steel, and porous titanium, as well as the ruthenium-titanium-tin oxide electrode just described.

The pump, illustrated as 16 in FIG. 1, is chosen to be compatible with the expected flow rate and to provide sanitary operation. Suitable pumps include tube pumps where the dialysate is impelled through a closed, flexible tube which provides a barrier to prevent undesired contamination. Other sealed pumps would also be suitable.

The power supply, illustrated as 18 in FIG. 1, can be a constant voltage or a constant current power source. The desired voltage will be above about 1.2 volts, preferably in the range from about 1.5 to 10 volts, with the voltage and current levels depending on the amount of dialysate being regenerated and on the specific cell design. With a coulombic efficiency of 50%, approximately $2 \times 10^4$ coulombs and 25 watts is required to oxidize each gram of the urea. A urea removal rate of 6 gm/hr with a 4 volt potential across the cell is typical.

Surface area of the anode is chosen to provide sufficient current density to produce the desired amounts of activated chlorine. The current density is generally between about 1 and 100 $mA/cm^2$ (based on cross-sectional area of the electrode), preferably between about 5 and 50 $mA/cm^2$ at the anode. The surface area of the cathode is less critical, although for flow-through cathodes it will generally be the same as that of the anode since the area will usually be defined by the cross-sectional area of the conduit. It should be noted that the surface areas of the preferred porous electrodes depend both on the total cross-sectional area as well as the porosity, i.e., the internal surface areas of the pores. For that reason, the current density and cross-sectional areas of the electrodes may vary within wide limits so long as sufficient activated chlorine species are produced.

The flow rate of dialysate through the cell depends on the application. When used as an integral part of a hemodialysis unit, the flow rate will usually correspond to the dialysis flow rate. When used to regenerate a spent pool of dialysis, the flow rate will be maximized to reduce the regeneration time. In either case, it will sometimes be desirable to provide multiple flow cells in parallel to increase the throughput through the system. The use of flow cells in parallel also allows optimization of the electrode area and flow rate through an individual cell while still providing a desired total throughput.

It is often desirable to place the electrolytic cell in series flow with one or more activated carbon beds. Such a bed upstream of the cell serves to remove substantially all major nitrogenous waste metabolites other than urea. The urea is then oxidized in the cell. An activated carbon bed downstream of the cell is useful to remove any residual chlorinated compounds which may pass from the cell.

In operation, chlorine and other oxidized chlorine species are generated at the anode by oxidation of chloride ion. The chlorine apparently reacts with urea, the primary nitrogenous waste metabolite, to form chlorinated intermediates in the vicinity of the anode. Evolution of chlorine at the anode has the further benefit that it can act as a steriliant for the dialysate.

The chlorinated intermediates may then be further oxidized and hydrolyzed to yield the desired end products, i.e., nitrogen and carbon dioxide. The oxidation and hydrolysis of the intermediates, however, is pH dependent and occurs much more readily under alkaline conditions. The separation of the anode and cathode creates two regimes or zones within the electrolytic cell. The anodic zone has an acidic pH (from the presence of hydronium ion resulting from the oxidation of water) which is compatible with the initial oxidation of urea to chlorinated intermediates. The region surrounding and within the cathode is more alkaline (from the presence of hydroxyl ion resulting from the reduction of water) which is compatible with the further degradation of the chlorinated intermediates to desired end products. The cathode reactions include hydrogen evolution, reduction of oxygen generated at the anode and reduction of the chlorine and activated chlorine species.

Thus, by separating the anode and cathode in the direction of flow, flowing the dialysate first by the anode and thereafter by the cathode, the degration of the organic wastes present in the dialysate is carried out in a highly efficient manner. Moreover, the oxidized inorganic chlorine species are substantially consumed by reaction with the urea, with any remaining oxidized chlorine species subject to reduction at the cathode. Chloride ion is regenerated by the reaction of the chlorinated intermediates in the vicinity of the cathode. Thus there is substantially no net generation of chlorine or other oxidized chlorine species by the subject method.

The method of the present invention enjoys particular utility in that the oxidized chlorine species (locally present at the anode) and the activated chlorine species will act as sterilants for the dialysate. The production of sterile dialysate is particularly important in continuous ambulatory peritoneal dialysis where use has been limited by problems with peritonitis.

The following experimental results are offered by way of example and not by way of limitation.

EXPERIMENTAL RESULTS

Experiment Nos. 1 and 2

A non-flow cell 40, as illustrated in FIG. 4, included an anode 42 comprising a flat sheet of ruthenium-titanium-tin oxide having an area of 21.4 cm² and a cathode 44 comprising a flat piece of platinum mesh. A separator 46 comprising Nafion ®425 membrane (perfluorsulfonic acid resin backed by Teflon ® mesh; DuPont, Wilmington, Del.) can be inserted to divide the interior of the cell 40 approximately in half. The separator 46 allows passage of sodium ion but prevents bulk mixing of anolyte and catholyte.

Phosphate-buffered saline (0.10M NaCl, pH 7.5) having a urea concentration of 0.50 g/l was electrolyzed in the cell 40 without the separator 46 at a current density of 28 mA/cm² (total current of 600 mA). The experiment was repeated with the separator 46 in place. The oxygen evolution, plotted over time, for each experiment is shown in FIG. 5. Oxygen evolution was not affected by the presence of the separator. The nitrogen evolution is similarly plotted in FIG. 6. Nitrogen evolution was markedly affected by the presence of the separator. Table 1 provides further results of the experiment.

TABLE 1

|  | Experiment 1 Without Separator | Experiment 2 With Separator |
|---|---|---|
| Initial pH | 7.5 | 7.5 |
| Initial [Urea] | 0.50 g/l | 0.50 g/l |
| Charge Passed | 3300 coul. | 2220 coul. |
| Final pH | 6.9 | 1.7 |
| Final Residual Chlorine* | $3 \times 10^{-4}$M | $1.4 \times 10^{-2}$M |
| Coulombic Efficiency for Oxygen Generation | 65% | 75% |
| Final [Urea] | 0.08 g/l | 0.32 g/l |
| Bulk Volume | 280 ml (anolyte and catholyte) | 150 ml (anolyte) |
| Urea Consumed | 2.0 ± 0.1 mmol | 0.48 ± 0.03 mmol |

TABLE 1-continued

|  | Experiment 1 Without Separator | Experiment 2 With Separator |
|---|---|---|
| Nitrogen Evolved | 2.2 ± 0.3 mmol | 0.30 ± 0.05 mmol |

*Residual chlorine was measured by addition of KI which releases chloride ion from nitrogen-bonded chlorine.

In Experiment 2 (as contrasted with Experiment 1), the pH became acidic, nitrogen evolution was suppressed, the residual chlorine level (indicative of N—Cl bonds or chlorinated intermediates) was substantially higher, and nitrogen evolution did not balance urea consumption. Such results indicate that chlorinated intermediates (created in the anode region) must be transported to regions of neutral or alkaline pH (such as the cathode region) for the rapid, quantitative oxidation and hydrolysis of urea to molecular nitrogen and carbon dioxide.

Experiment No. 3

A second experimental system was set up as illustrated in FIG. 7. A flow cell 50 comprised a glass cylinder 52 (2.5 cmID × 30 cm) open at each end to define a flow path for the dialysate. A tube pump 54 was connected to supply experimental solution from an Erlenmeyer flask 56 to one end of the flow cell 50. A magnetic stir bar 58 was provided to agitate the experimental solution in the flask 56. The outlet end of the flow cell 50 was connected to return the experimental solution to the flask 56. Porous, flow-through ruthenium-titanium oxide electrodes prepared as described hereinabove were provided as an anode 60 and cathode 62. The electrodes each extended across the flow path defined by the cylinder 52 and had an exposed surface area of 4.9 cm². Sampling ports 64 were provided where indicated. The distance d between the anode and cathode was 5.6 cm.

The experimental solution was a phosphate buffered saline solution (1.0M Na₂SO₄, 0.10M NaCl, pH 7.0) having 0.50 g/l urea. The solution (719 ml) was added initially to the flask 56 and pumped through the system at a rate of 0.18 ml/sec.

A constant current of 340 mA was applied to the anode and cathode by a power supply 58. This related to an anode potential of approximately 1.155 volts based on the standard Calomel electrode. Current was on from 0–7600 seconds and 7700–9150 seconds.

Referring now to Table 2, liquid samples were taken from sample port 64a located between the electrodes and sample port 64b located downstream of the flow cell 50 at the times indicated. The urea concentration was determined by the standard colorimetric diacetyl monoxine assay. As expected, the urea concentration decreased with time in the circulating experimental solution. The presence of chlorinated intermediates was determined by examining the ultraviolet absorbance of the sample at 244 nm and by measuring the residual chlorine level by titration with potassium iodide.

TABLE 2

| | | Liquid Sample Composition | | | | |
|---|---|---|---|---|---|---|
| Sample No. | Time (Sec) | Location | Urea** (g/l) | pH | Residual Chlorine (moles/l) | Intermediates |
| 1* | 0 | flask | 0.5 | 6.75 ± 0.05 | 0 | none |
| 2 | 3600 | 64b | 0.475 | 6.93 ± 0.05 | $5 \times 10^{-5}$ | dichlorourea |
| 3 | 5250 | 64a | ND | 3.18 ± 0.03 | $4 \times 10^{-4}$ | monochlorourea and dichloroura |
| 4 | 7600 | 64a | ND | 3.19 ± 0.03 | $5 \times 10^{-4}$ | monochlorourea |

TABLE 2-continued

| | | Liquid Sample Composition | | | | |
|---|---|---|---|---|---|---|
| Sample No. | Time (Sec) | Location | Urea** (g/l) | pH | Residual Chlorine (moles/l) | Intermediates |
| 5 | 8900 | 64b | 0.449 | 7.13 ± 0.03 | $7 \times 10^{-5}$ | and dichlorourea monochlorourea |
| 6 | 10,500 | flask | 0.445 | 6.86 ± 0.03 | $1 \times 10^{-4}$ | monochlorourea |

*Analysis prior to treatment
**ND: not done.

This example shows that electrolysis was porous, flow-through electrodes of the preferred composition results in: (1) urea oxidation; (2) creation of an acidic electrolyte between the anode and cathode; (3) neutralization (to pH~7) of said acidic electrolyte by subsequent passage through the cathode; (4) creation of substantial levels of chlorinated intermediates ($\sim 5 \times 10^{-4}$ moles/l as measured by the residual chlorine assay) by passage of the solution through the anode (samples 3 and 4); and (5) a decrease by a factor of five or greater in the levels of chlorinated intermediates by subsequent passage of the solution through a porous, flow-through cathode (samples 5 and 6).

Composition of the electrolysis product gas from sample port 64c was determined using a Hewlett Packard model 5830A gas chromatograph equipped with a thermal conductivity detector. The column ($\frac{1}{8}$-inch OD stainless steel) was packed with Molecular Sieve 5A. Headspace in the flask was initially filled with air. Data on gas composition at steady state are presented in Table 3.

TABLE 3

| | | Gas Composition | |
|---|---|---|---|
| Time Interval | | $N_2/O_2$ | |
| (sec) | No. Samples | Actual | Theoretical* |
| 4530-10,070 | 7 | 0.08 ± 0.03 | 0.09 |

*Theoretical $N_2/O_2$ was calculated from observed decrease in urea concentration and assumption that oxygen evolution constitutes remainder of anodic charge passed.

The results in Table 3 show that the expected amount of nitrogen (from urea oxidation) was observed in the product gas. Thus, the data are consistent with the proposed mechanism for urea degradation in a saline solution. A significant amount of urea was, in fact, oxidized. Chlorinated intermediates produced in the vicinity of the anode were destroyed in the vicinity of the cathode. Therefore, porous flow-through electrodes in an anode to cathode flow configuration provide an efficient method for quantitatively oxidizing nitrogen-containing waste metabolites, such as urea, to molecular nitrogen.

Although the foregoing invention has been described in some detail by way of illustration and example for purposes of clarity and understanding, it will be obvious that certain changes and modifications may be practiced within the scope of the claims.

What is claimed is:

1. A method for regenerating hemodialysate by oxidizing urea-containing organic wastes removed from human blood, said method utilizing a cell defining a flow path for said hemodialysate and having a porous, flow-through anode and a cathode spaced apart in a direction of hemodialysate flow through the flow path, said method comprising:

flowing the hemodialysate containing the urea through the cell in a direction from the anode to the cathode so that a major portion of the hemodialysate will pass the anode prior to passing the cathode while maintaining a sufficient electrical potential difference between the anode and cathode to oxidize chloride present in the hemodialysate to chlorine, whereby the urea present is degraded to nitrogen and carbon dioxide and the regenerated hemodialysate is substantially free of chlorine as other than chloride as a result of reduction of the remaining chlorine at the anode.

2. A method as in claim 1, wherein the anode material is selected from stabilized platinum group metals, mixed stabilized noble metal oxides and carbon.

3. A method as in claim 1, wherein the anode is ruthenium-titanium-tin oxide or a stabilized noble metal oxide deposited on a titanium substrate.

4. A method as in claim 1, wherein the cathode material is selected from platinum, nickel, cadmium, tin, stainless steel, porous titanium and ruthenium.

5. A method as in claim 1, wherein the potential between the anode and cathode is above about 1.2 volts.

6. A method as in claim 1, wherein the potential between the anode and the cathode is in the range from about 1.5 to 10 volts.

7. A method as in claim 1, wherein the potential difference is sufficient to provide a current density in the range from about 1 to 100 mA/cm² (based on cross-sectional area of the anode) at the anode.

8. A method as in claim 1, wherein the anode is a porous, flow-through ruthenium-titanium-tin oxide electrode.

9. A method as in claim 1, wherein the anode is a platinum, wire mesh electrode.

10. A method as in claim 1, wherein the anode and cathode are both porous, flow-through ruthenium-titanium-tin oxide electrodes.

11. A method as in claim 1, wherein the flow path is linear and the anode and cathode are arranged in series.

12. A method as in claim 1, wherein the flow path is radial and the anode and cathode are flow-through concentric cylinders.

13. A method as in claim 1, wherein the anode and cathode are flow-through electrodes and arranged as nested thimbles.

* * * * *